United States Patent
Vignaud et al.

(10) Patent No.: US 9,848,974 B2
(45) Date of Patent: Dec. 26, 2017

(54) SAFETY CARTRIDGE FOR A REMOVABLE VENA CAVA FILTER

(75) Inventors: Alain Vignaud, Quincay (FR); Dan Gutknecht, Jaunay Clan (FR); Simon Forber, Liguge (FR)

(73) Assignee: B. Braun Medical SAS (FR)

( * ) Notice: Subject to any disclaimer, the term of this patent is extended or adjusted under 35 U.S.C. 154(b) by 1665 days.

(21) Appl. No.: 13/500,655

(22) PCT Filed: Oct. 6, 2010

(86) PCT No.: PCT/EP2010/006096
§ 371 (c)(1),
(2), (4) Date: Nov. 12, 2015

(87) PCT Pub. No.: WO2011/042163
PCT Pub. Date: Apr. 14, 2011

(65) Prior Publication Data
US 2016/0184074 A1    Jun. 30, 2016

(30) Foreign Application Priority Data
Oct. 6, 2009 (FR) ..................... 09 04780

(51) Int. Cl.
*A61F 2/01* (2006.01)
*A61F 2/00* (2006.01)
*A61B 90/00* (2016.01)

(52) U.S. Cl.
CPC .............. *A61F 2/0095* (2013.01); *A61F 2/01* (2013.01); *A61F 2/013* (2013.01); *A61B 2090/0801* (2016.02); *A61F 2002/011* (2013.01); *A61F 2002/016* (2013.01); *A61F 2230/005* (2013.01); *A61F 2230/0065* (2013.01); *A61F 2230/0067* (2013.01)

(58) Field of Classification Search
CPC ....... A61F 2/013; A61F 2/01; A61F 2002/011
USPC .......................................... 206/363; 606/108
See application file for complete search history.

(56) References Cited

U.S. PATENT DOCUMENTS

| | | | |
|---|---|---|---|
| 2002/0045918 A1 | 4/2002 | Suon | |
| 2004/0087999 A1* | 5/2004 | Bosma | A61F 2/01 606/200 |
| 2004/0088002 A1* | 5/2004 | Boyle | A61F 2/013 606/200 |
| 2005/0080449 A1 | 4/2005 | Mulder | |

(Continued)

FOREIGN PATENT DOCUMENTS

| | | |
|---|---|---|
| CN | 2640421 Y | 9/2004 |
| CN | 101389289 A | 3/2009 |

OTHER PUBLICATIONS

Original Chinese Language First Official Action.
English Language Translation of First Official Action.

*Primary Examiner* — King M Chu
(74) *Attorney, Agent, or Firm* — RatnerPrestia

(57) ABSTRACT

The invention relates to a safety cartridge (1) for a removable vena cava filter (20), having a proximal end (2) and a distal end (3) and having an inner channel (4) extending between the ends. The cartridge is characterized in that it comprises, on the distal end (3) thereof, a linking device (5) for forming a link with a catheter (30) and, in the inner channel thereof, a projection (6) having a limited size in the axial direction of the cartridge (1) so as to locally reduce the cross-section of the channel (4).

10 Claims, 4 Drawing Sheets

(56) References Cited

U.S. PATENT DOCUMENTS

2005/0251197 A1* 11/2005 Hensley .................. A61F 2/01
  606/200
2009/0131970 A1    5/2009 Chanduszko

* cited by examiner

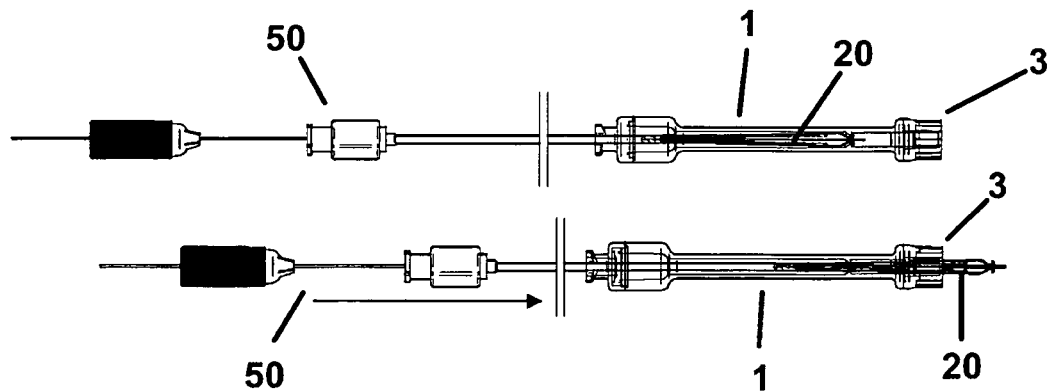
Fig. 6a
Fig. 6b
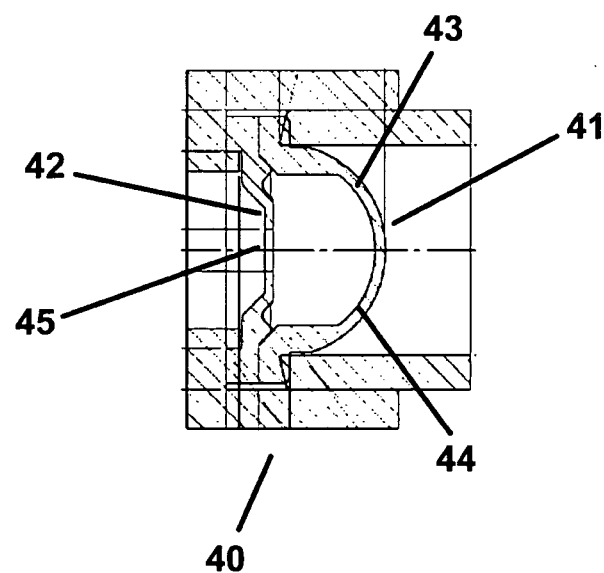
Fig. 7

SAFETY CARTRIDGE FOR A REMOVABLE VENA CAVA FILTER

The present invention relates to a safety cartridge for a removable vena cave filter.

Vena cave filters are used for the prevention of pulmonary emboli. To that end, a filter, which can be folded, is introduced into the vein by means of a catheter, most often into the lower vena cava so to prevent blood clots from running up towards the pulmonary artery. Removable filters are designed for a temporary usage, for example, during surgical interventions, and to be removed thereafter. They may also be left in place in the patient if his condition requires a permanent protection.

The filters can be folded so that they can be inserted in folded condition into the inner channel of a catheter and placed into a vein by means of said catheter. The distal end of the catheter is placed at the insertion point desired for the filter and the latter is then extracted from the catheter. To that end, the filter is generally held in its position relative to the vein thanks to a holding device and the catheter is then removed gradually. The folded filter inside the catheter unfolds when exiting the distal end of the catheter and is deployed inside the vein.

A current kind of filter consists of legs in the form of metal wires which can be opened into a fan, regrouped on the proximal end. In the folded condition, inside the catheter, the legs are under tension and oriented approximately parallel to one another. Outside the catheter, due to their elasticity, the legs move apart so that the filter can be deployed in the vein. A few legs at least have, on their ends, barbed hooks with which the filter may anchor into the walls of the blood vessel.

To be removed, the filter has a hook on its proximal end or another gripping means. A catheter can then be inserted into the vein up to the position of the filter. The filter is captured by a corresponding device, which can be a "lasso" or another suitable system. To separate the filter from the walls of the vessels, the catheter should be pushed further in the distal direction, whereas the filter is held in its position by the capturing device. The more the filter is covered with the catheter, the more its legs are compressed. The ends of the legs and the barbed hooks are separated from the wall of the vessel and the filter can be accommodated completely in the catheter, and subsequently removed by the latter in the proximal direction.

To prevent the barbed hooks from anchoring at the distal end of the catheter, the legs fitted with barbed hooks are generally slightly folded back inwardly on the end, so that the barbed hooks do not project onto the external contour when the filter is folded and cannot be anchored on the catheter.

According to the state of the art, the filter is totally removed from the inner channel of the catheter so that the latter, still in the vein, can be used before its retraction for other tests. Seen in this light, the filter is deployed immediately when leaving the catheter and once in open air exposes its attachment means. Due to their aggressiveness, the barbed hooks cause injury to the nursing staff by pricking. In the same manner, the filter can, by being deployed abruptly, cause blood splashing which may be contaminated. There is consequently a high risk of contamination when devices are soiled by the blood, either by pricking or by splashing.

The aim of the present invention is to realise a device for retracting a removable vena cave filter from a blood vessel, which reduces the risk of injury for the nursing staff.

This task is solved through a so-called safety cartridge according to claim 1. Advantageous embodiments may be found in the dependent claims 2 to 7.

The safety cartridge for removable vena cave filters in accordance with the invention includes a proximal end, a distal end and an inner channel extending between the ends. It is characterised in that it comprises on its distal end, a linking device for connection to a catheter. It moreover comprises, in its inner channel, a projection having a limited size in the axial direction of the cartridge so as to locally reduce the cross-section of the channel. Said projection is preferably spaced apart from the ends of the cartridge.

A safety cartridge of such type can be connected with its linking device to the proximal end of a venous catheter to remove a vena cave filter. The filter can then be captured as known with a conventional device such as a lasso and retracted into the distal end of the catheter. Through the catheter, the filter is then inserted into the cartridge which is arranged on the proximal end of the catheter. The proximal end of the filter is pulled with the capturing device through the channel of the cartridge and passes the projection. However, the outwardly oriented hooks of the legs are anchored on the shoulder of the projection and limit the displacement of the filter inside the cartridge. The filter cannot be removed from the cartridge on the proximal side any longer. There is no risk of injury for the nursing staff. There is no danger of injury on the hooks or by contamination by blood splashing.

The cartridge containing the filter connected to the retraction system may then be separated from catheter by means of the linking device. The catheter can stay in the vein, for example, to perform a control cavography.

Independently, the filter can be extracted from the cartridge by pushing it towards the distal end of the latter by using the retraction system. The filter can then be collected in a sampling box, then disengaged from the retraction system, which can for example be a lasso.

The safety cartridge can have on its proximal end a sealing system. The latter may be formed of one or several hemostatic valves or be a gland-type system. Such a system can for example be composed of two valves mounted in series. In this case, a first split valve ensures tightness by the contact of both lips when the retraction device is not inserted. A second valve, with a bore of appropriate diameter, for its own part ensures tightness when the retraction system runs therethrough. The system then seals the cartridge in the presence and in the absence of the retraction system.

The linking device for connecting the cartridge to a catheter may be, for example, a screw link or a bayonet link. It may also, advantageously, include a Luer-type "cone/cone" link.

The projection can be ring-shaped so as to extend locally along the whole circumference of the channel. Depending on the filter used, it may however be also sufficient if the projection only extends over a portion of the circumference. The projection can be continuous or discontinuous.

Preferably, the projection comprises on the distal side a shoulder forming an angle smaller than 150° with the greater axis of the cartridge. That angle is preferably smaller than 135° and especially approximately rectangular. The shoulder may also exhibit an angle smaller than 90° on its distal side and especially form an acute angle with the greater axis of the cartridge. This way, the hooks on the legs of the filter can be anchored in the projection and do not slip. The filter is securely held in the cartridge and cannot be pulled out of the cartridge in the proximal direction.

The cartridge is advantageously dimensioned so that the distance between the projection and the sealing system of the cartridge is greater than the total length in folded condition of the portion of the filter situated between its proximal end and its anchoring means. The filter thus remains fully contained in the cartridge, and only the retraction system is passed through the sealing system. The tightness of the cartridge is then not compromised.

The cartridge can be advantageously a moulded part, manufactured according to an injection-moulding method.

An embodiment of the invention is described in more detail below using the appended figures, among which:

FIGS. 6a and 6b show diagrammatically, in cross-section, the removal of a filter from the cartridge;

FIG. 7 shows, in cross-section, a sealing system comprising valves for the proximal end of a cartridge;

Figure 1:
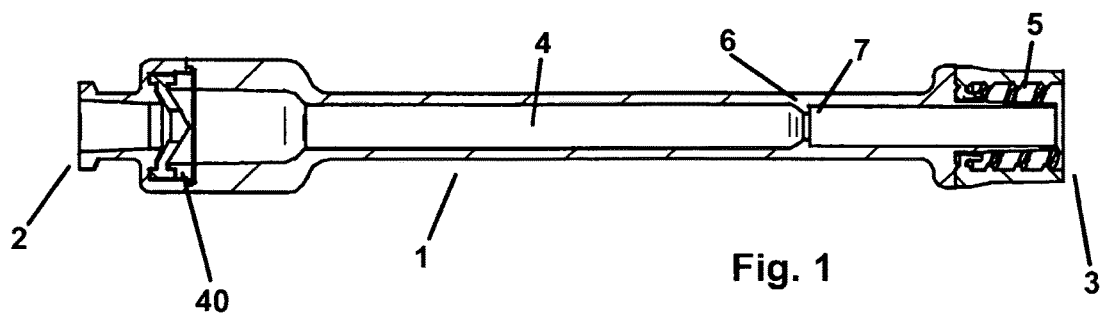
FIG. 1 shows a safety cartridge according to the invention in cross-section.

FIG. 1 shows a safety cartridge 1 according to the invention in cross-section. The cartridge 1 has a proximal end 2 and a distal end 3. An inner channel 4, in this example substantially cylindrical, extends between the ends 2, 3. The cartridge 1 comprises on its distal end 3, a thread 5 to link the cartridge 1 with a catheter. In its channel 4, the cartridge 1 comprises a projection 6 having a limited size in the axial direction of the cartridge so as to reduce the inner diameter of the channel 4. The shoulder 7 of the projection 6 on the distal side is perpendicular to the inner wall of the channel 4. On the proximal side, the projection 6 is slightly tilted towards the inner wall.

The safety cartridge 1 comprises, in addition, a sealing system 40 on its proximal end containing two hemostatic valves.

Figure 2:
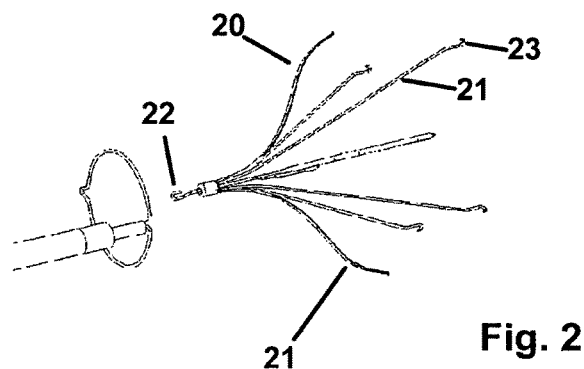
FIG. 2 shows a removable vena cave filter of a type which may be removed using the safety cartridge according to the invention, when it is deployed, in a perspective representation.

FIG. 2 shows a removable vena cave filter 20 of a type which may be removed using the safety cartridge according to the invention, deployed and in a perspective representation. The filter 20 comprises a multitude of legs 21 which are regrouped into a bundle on the proximal side and move apart relative to one another in the distal direction when the filter is deployed. The filter 20 has a hook 22 on the proximal side. Some of the legs 21 possess on their ends barbed hooks 23 which are oriented outwardly and are anchored in the wall of the vessel to position the filter 20 reliably.

Figure 3:
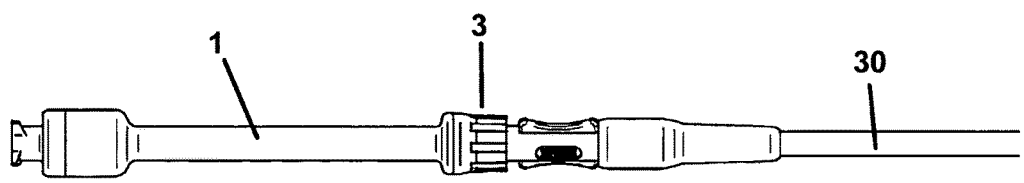
FIG. 3 shows a safety cartridge according to the invention in a lateral view in connection with a catheter.

FIG. 3 shows a safety cartridge 1 according to the invention in a lateral view in connection with a catheter 30. The linking device 5 provides a removable connection between the cartridge 1 and the catheter 30.

Figure 4A:
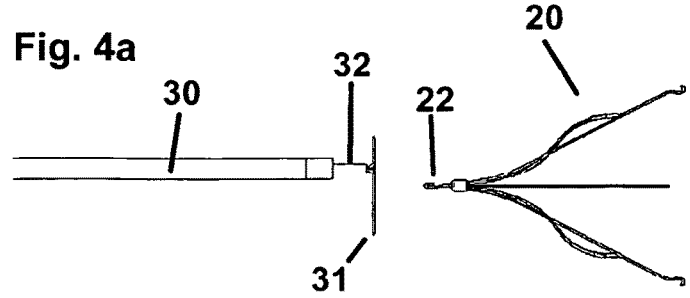
FIGS. 4a to 4f shows the progressive retraction of the filter of FIG. 2 from a blood vessel.
Figure 4B:
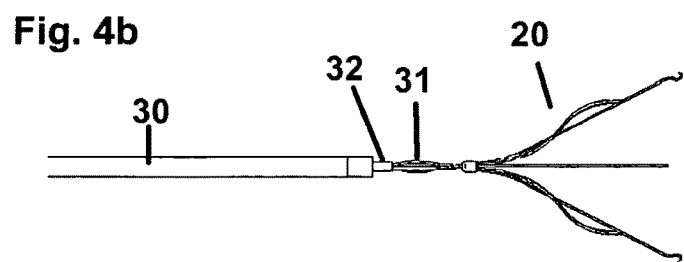
Figure 4C:
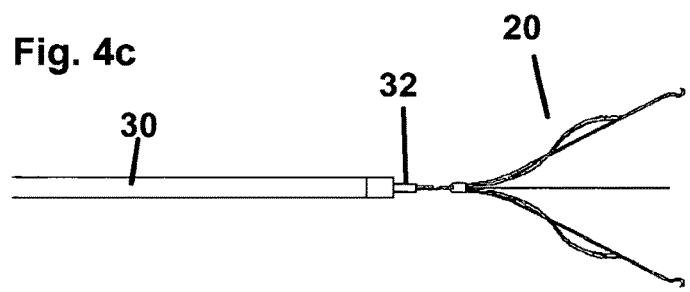
Figure 4D:
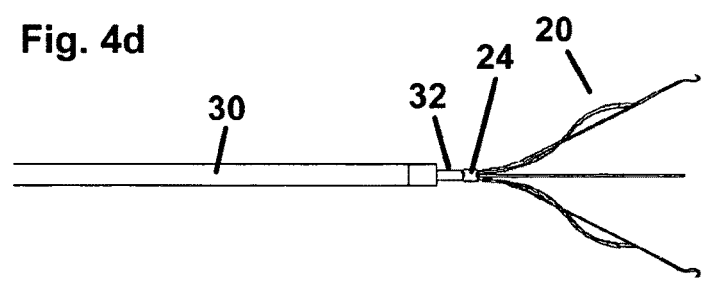
Figure 4E:
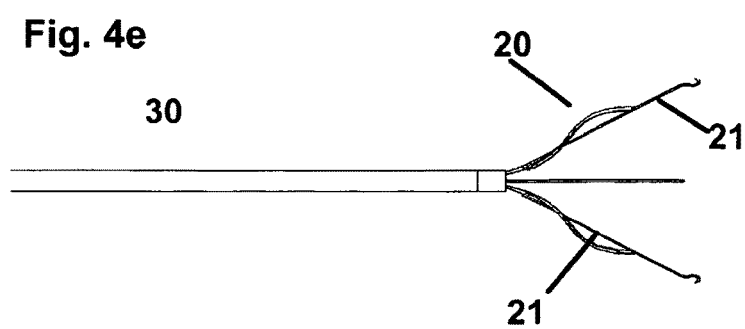
Figure 4F:

FIGS. 4a to 4f show the distal end of a catheter 30 comprising a device intended for extracting a removable vena cave filter from a blood vessel, in that particular instance a lasso in this description, as well as progressive retraction of a filter 20. The catheter 30 comprises a metal wire with a loop made of metal wire 31, said lasso. The metal wire is guided in a sleeve 32 situated inside the catheter 30. The sleeve 32 may move inside said catheter. The filter to be explanted must be located. After that, the catheter 30 is inserted into the blood vessel (not represented) up to the position of the filter 20. The lasso 31 is released from the distal end of the catheter 30 (FIG. 4a). The hook 22 of the filter 20 is captured with the lasso 31. The sleeve 32 is then descended in the distal direction so as to close the lasso 31 (FIG. 4b). The sleeve 32 is pushed further in the distal direction (FIG. 4c) until the hook is received in the sleeve and the head 24 of the filter 20 is held securely (FIG. 4d). The sleeve 32 is then held in this position and the catheter 30 is moved in the distal direction so as to slip over the filter 20 (FIG. 4e) and the legs 21 of the filter fold up (FIG. 4f).

Figure 5:
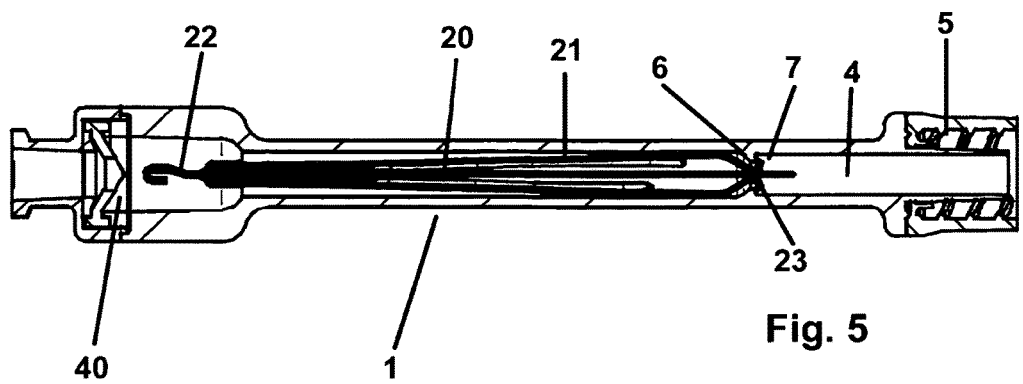
FIG. 5 shows a safety cartridge according to FIG. 1 in cross-section which includes a filter removed from a blood vessel.

FIG. 5 shows a safety cartridge 1 according to FIG. 1 in cross-section which includes an explanted filter 20. It can be seen that the filter 20 is pulled on its hook 22 into the channel 4 of the cartridge 1. The barbed hooks 23 on the legs 21 of the filter are thus anchored in the shoulder 7 of the projection 6.

The legs 21 of the filter 20 carrying the barbed hooks 23 are slightly folded inwardly on their ends so that the hooks 23 do not project over the contours of the filter when the filter 20 folds up and so that the filter can be inserted into the catheter. The contour of the projection 6 hence advantageously follows the contour of the legs of the filter 21 to ensure proper anchoring of the hooks 23 on the projection 6.

The projection 6 in the channel 4 is arranged so that the distance between the projection 6 and the sealing system 40 of the cartridge is greater than the total length, in folded condition, of the portion of the filter 20 located between the proximal end and the anchoring means 23 thereof. The filter 20 thus remains fully contained in the cartridge 1, and only the retraction system is passed through valves of the sealing system 40. The tightness of the cartridge 1 is then not compromised. The cartridge 1 can be removed from the catheter via the linking device 5 and eliminated. There is no risk of injury for the nursing staff. The catheter 30 may still remain in the blood vessel after retraction of the filter 20 for carrying out a control cavography if required.

FIG. 6a shows the cartridge 1 removed from the catheter according to FIG. 5 with its retraction system 40 for the filter 20. The filter 20 can be extracted from the cartridge 1 (FIG. 6b) by pushing it towards the distal end 3 of the latter by using the retraction system 40. The filter can then be collected in a sampling box (not represented), then disengaged from the retraction system 50, which can for example be a lasso.

The sealing system 40 represented in FIG. 7 is composed of two valves 41, 42 mounted in series. A first split valve 41 ensures tightness by the contact of both lips 43, 44 when the retraction device is not inserted. A second valve 42, with a bore 45 of appropriate diameter, for its own part ensures tightness when the retraction system runs therethrough. The system 40 is mounted on the proximal end of the cartridge and then seals the cartridge in the presence and in the absence of the retraction system.

Figure 8:
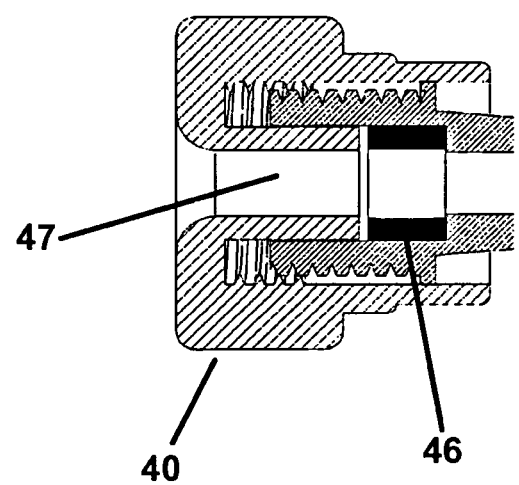
FIG. 8 shows, in cross-section, a sealing system of gland type for the proximal end of a cartridge.

FIG. 8 shows, in cross-section, a gland-type sealing system 40. The system includes an O-ring 46 around the passageway 47 of the retraction system for sealing the system when the retraction system is in place.

The invention claimed is:
1. A safety cartridge for a removable vena cave filter, the safety cartridge having a proximal end and a distal end and having an inner channel extending between the ends,
wherein the safety cartridge comprises on its distal end a linking device for forming a link with a catheter, and in the inner channel thereof a projection so as to locally reduce the cross-section of the channel, whereas the projection is spaced apart from the ends of the cartridge; and the projection comprises on its distal side a shoulder forming an approximately rectangular angle or an acute angle.

2. A safety cartridge according to claim 1, wherein the cartridge comprises on its proximal end a sealing system having one or several hemostatic valves or a gland-type sealing system.

3. A safety cartridge according to claim 1, wherein the linking device is a screw link.

4. A safety cartridge according to claim 1, wherein the projection has an annular, continuous or discontinuous shape.

5. A safety cartridge according to claim 1, wherein the cartridge is a moulded part.

6. A safety cartridge according to claim 1, wherein the proximal side of the projection is tilted towards the inner wall.

7. A safety cartridge according to claim 1, wherein the linking device is arranged on the outer side of the distal end of the cartridge.

8. A safety cartridge according to claim 1, wherein the cartridge is removably arranged on a proximal end of the catheter.

9. A safety cartridge for a removable vena cave filter having a proximal end and a distal end and having an inner channel extending between the ends, wherein the safety cartridge comprises on its distal end a linking device for forming a link with a catheter, and in the inner channel thereof a projection so as to locally reduce the cross-section of the channel whereas the projection is spaced apart from the ends of the cartridge; and the proximal side of the projection is tilted towards the inner wall.

10. A safety cartridge for a removable vena cave filter having a proximal end and a distal end and having an inner channel extending between the ends, wherein the safety cartridge comprises on its distal end a linking device for forming a link with a catheter, whereas the linking device is arranged on the outer side of the distal end of the cartridge; and in the inner channel thereof a projection having a limited size in the axial direction of the cartridge so as to locally reduce the cross-section of the channel whereas the projection is spaced apart from the ends of the cartridge.

* * * * *